United States Patent [19]

Liu et al.

[11] Patent Number: 4,972,957
[45] Date of Patent: Nov. 27, 1990

[54] PARTICLE CONCENTRATING SAMPLER

[75] Inventors: Benjamin Y. H. Liu, North Oaks; Virgil A. Marple, Maple Plain, both of Minn.

[73] Assignee: Regents of the University of Minnesota, Minneapolis, Minn.

[21] Appl. No.: 249,716

[22] Filed: Sep. 27, 1988

[51] Int. Cl.$^5$ ................................. B07B 7/00
[52] U.S. Cl. ........................ 209/143; 55/510; 72/28.05
[58] Field of Search .......... 209/143, 142, 136, 132, 209/133, 134, 135, 138, 139.1; 73/28, 865.5; 55/510

[56] References Cited

U.S. PATENT DOCUMENTS

| | | | |
|---|---|---|---|
| 3,606,733 | 9/1971 | Arstikaitis | 55/270 X |
| 3,901,798 | 8/1975 | Peterson | 209/143 |
| 4,133,202 | 1/1979 | Marple | 73/28 |
| 4,301,002 | 11/1981 | Loo | 209/143 |
| 4,590,792 | 5/1986 | Chiang | 73/28 |
| 4,670,135 | 6/1987 | Marple et al. | 209/143 |
| 4,767,524 | 8/1988 | Yeh et al. | 209/143 |

FOREIGN PATENT DOCUMENTS

| | | | |
|---|---|---|---|
| 208644 | 12/1983 | Japan | 73/28 |
| 2179273 | 3/1987 | United Kingdom | 209/143 |

Primary Examiner—Donald T. Hajec
Attorney, Agent, or Firm—Kinney & Lange

[57] ABSTRACT

A particle concentrating sampler utilizes a virtual impactor, which is an inertial classifier, for concentrating airborne particles above a cut size into a smaller volume air. The concentrated particles are counted, or collected on impactor plates or by using other collection techniques, such as filters or electrostatic precipitators. The concentration of the larger particles which are of interest for analysis insures that the number of particles, particularly in clean room environments, is sufficient so that a significant sampler or count can be obtained without sampling large volumes of air.

6 Claims, 3 Drawing Sheets

PARTICLE CONCENTRATING SAMPLER

BACKGROUND OF THE INVENTION

1. Field of the Invention

The present invention relates to aerosol particle concentration using virtual impactors for the concentrator.

2. Description of the Prior Art

The sampling of atmospheric aerosols utilizing virtual impactors is known. For example, U.S. Pat. No. 4,670,135 shows a high volume virtual impactor that utilizes nozzles that are arranged with passageways to divide the air flow into major flows and minor flow. The larger mass airborne particles have inertia such that they pass through a receiving tube to a filter while the major flow of air and the smaller particles are diverted laterally.

Also, the use of an impactor plate for receiving impinging particles has been known in the prior art. Concentrating the particles by inertial separation and then counting or collecting the larger particles in a single, effective assembly is still lacking in the art.

SUMMARY OF THE INVENTION

The present invention relates to a particle concentrating sampler and collector, which in one specific form shown includes an impactor plate or plates on which the particles can be collected, after concentration. The concentrated particles then can be analyzed in a manner desired.

In one form shown, a nozzle receives the major flow that is a known volume with a suitable blower or fan. The major air flow is diverted laterally after passing through the nozzle and the inertia of the larger particles carries them into a receiving tube aligned with the nozzle. Only a small percentage of the total volume of air through the nozzle is allowed to pass through the receiving tube, which is a "minor flow" that is also controlled by a pump. Usually, the minor flow is less than 10% of the major flow, and in the form shown, is about 5% of the major flow.

The receiving tube is made so that it is larger than the nozzle and the major flow must reverse or change its direction. Any part of the major flow that enters the receiving tube flows out the entrance of the receiving tube near the outer walls of the tube. The larger particles have enough inertia to penetrate into the receiving tube and exit with the minor flow.

Smaller particles that do not have as much inertia will not penetrate as far into the receiving tube and will be carried out with the major flow. There will always be some small particles in the minor flow. The concentration of the small particles will be the same for both the major and minor flows, but since the minor flow is only a small fraction of the total flow (for example, 5%), only 5% of the small particles in the total flow will be sampled in the minor flow while the majority of the large particles carried in the total flow will now be concentrated in the minor flow.

The minor flow will then be directed to a desired function, for example onto an impactor plate as shown in one form of the invention. As shown, two stages of impactor plates for collecting the larger particles before filtering are used. In addition, various types of particle counting instruments, such as optical particle counters can be used, or collection can be done with an electrostatic precipitator receiving the minor flow.

Essentially, the "cut size" of the particles can be determined by arrangement of the nozzles and receiving tubes. The cut size is defined as the minimum size particle at which 50% of the particles passing through the nozzle are collected in the minor flow. The cut size can be varied by changing parameters such as the nozzle size or the flow rate through the nozzle. Normally, the cut size is in the range of 1–10 micron diameter size range, but by special design the cut size can be smaller or larger.

In one form of the present invention, collection devices are shown as impactor plates that are mounted onto electon microscope studs, so that upon disassembly of the concentrator device, the impactor plates can be removed and placed directly on an electron microscope for analysis. Suitable filters are provided, and the particles collected on the filters also can be analyzed.

The present device including the collector is especially adapted for use in relatively clean air that may exist in atmospheres such as in clean rooms, because of the relatively low number of particles. By concentrating the volume before collection of particles, the particles can be concentrated to a smaller area and the collection velocity can be decreased with the decreasing flow rate. Where impaction plates are used, the number of particles that bounce off the impactor plate can likewise be reduced.

The sampling air volumn is of the minor flow, which will be only a small fraction of the flow entering the nozzle, but the minor flow will contain almost all of the particles larger than the cut size of the virtual impactor. Particles smaller than the cut size are generally not of interest in the collector, although they can be collected on a filter and analyzed easily.

By way of example, if the clean room air has one large particle per cubic foot, by concentrating it with a 5% minor flow, the particles of interest will be increased to 20 particles per cubic foot. The flow rate that is desired through an optical particle counter is about 1 cubic foot per minute, and with a minor flow of 1 cubic foot per minute. There would be 10 particles each minute. This means that the particle counting can occur much faster. Reconcentrating the flow even more, so that the minor flow will be 1% of the major flow for example, 100 particles per minute could be sent through a standard optical particle counter each minute.

BRIEF DESCRIPTION OF THE DRAWINGS

FIG. 1 is a vertical sectional view through a typical virtual impactor used as a particle concentrating and collecting device made according to the present invention;

FIG. 2 is a top plan of the device of FIG. 1 taken as on line 2—2 in FIG. 1;

FIG. 3 is a sectional view taken as on line 3—3 in FIG. 1;

FIG. 4 is a sectional view taken as on line 4—4 in FIG. 1;

FIG. 5 is a sectional view taken as on line 5—5 in FIG. 1;

FIG. 6 is a sectional view taken as on line 6—6 in FIG. 1;

FIG. 7 is a schematic representation of the virtual impactor stage shown in the device of FIG. 1, with the minor flow being sent through a particle counting instrument, such as an optical particle counter; and FIG. 8 is a schematic representation similar to FIG. 7, showing an electrostatic precipitator for collecting the particles in the minor flow.

DETAILED DESCRIPTION OF THE PREFERRED EMBODIMENTS

Figure 2:
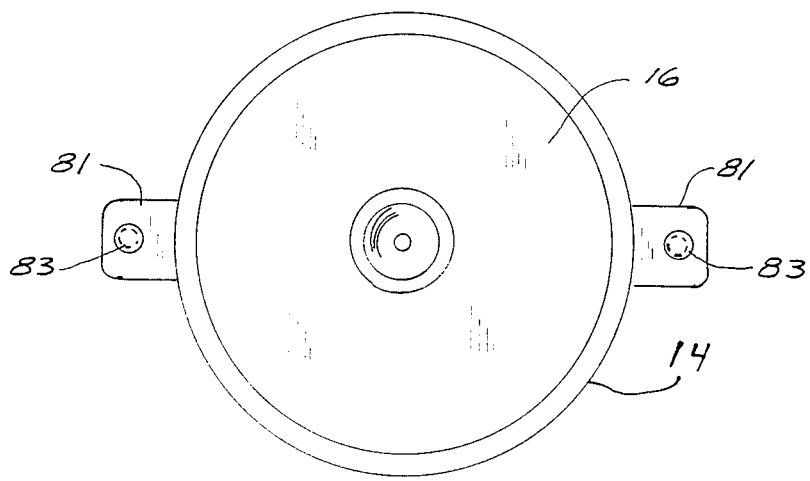
Figure 3:
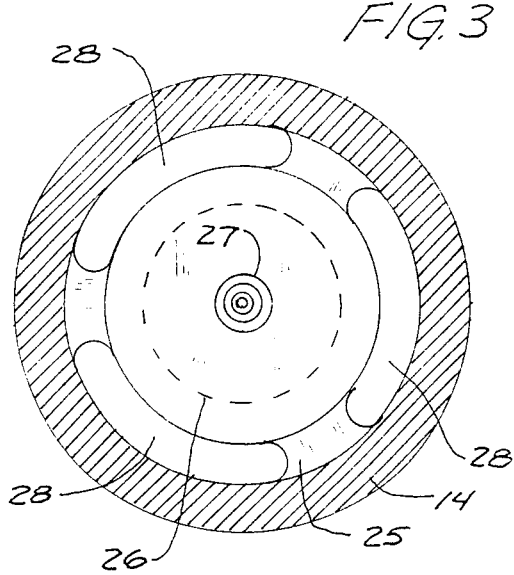

A particle concentrating sampler and collector indicated generally at 10 has an outer housing assembly 11, which includes a base 12, a multi-shouldered intermediate section 13, and a cap or upper housing 14. The upper housing 14, as can be seen in FIG. 2 as well, is cylindrical and defines an interior chamber, and has a top wall 16 that includes an inlet nozzle 17. The nozzle 17 has a Venturi shape, and has an outlet orifice 18 centered on a central axis indicated at 19. The interior chamber 22 of housing 14 is cylindrical, and a cylindrical first stage virtual impactor housing indicated at 23 is supported in interior chamber 22 through a plurality of radial webs (see FIGS. 3 and 4, for example) indicated at 25.

The first stage virtual impactor housing 23 has an upper wall 26 in which a receiver tube 27 is mounted. Receiver tube 27 is axially centered on the central axis 19 and thus is aligned with the nozzle. The webs 25 are spaced annularly and support the virtual impactor housing 23 so that there are passageways indicated at 28 formed in three part-annular sections. The passageways 28 lead into an annular passageway 30 that surrounds a second stage impactor housing 32.

Figure 4:
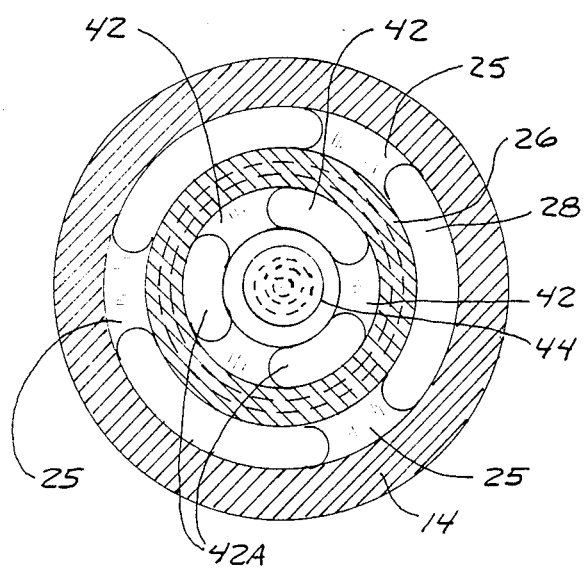

The second stage impactor housing 32 is supported on a base sleeve member 33. The base member 33 and second stage impactor housing 32 both have cylindrical outer surfaces that are substantially the same diameter as the outer cylindrical surface of the first stage virtual impactor housing 23. The base sleeve member 33 is supported on a boss 37 of the intermediate section 13. The housing 33 is bored out to provide a flange or skirt 38 that fits around the boss 37, and the skirt is sealed on the outer surface of the boss with a suitable "0"-ring 39. The intermediate or second stage impactor housing 32 as shown has an interior support plate 41 that is supported relative to the outer peripheral wall of the second stage impactor housing 32 through a plurality of annularly spaced webs 42, as can be seen in FIG. 4. The plate 41 in this form of the invention is centered on the axis 19, and has a receptacle for receiving a headed stud from an electron microscope that has a tang 43. The head forms an impactor plate 44. The tang 43 and impactor plate 44 can be transferred from the concentrating sampler and collector directly to an electron microscope so that particles collected thereon can be analyzed.

Figure 5:
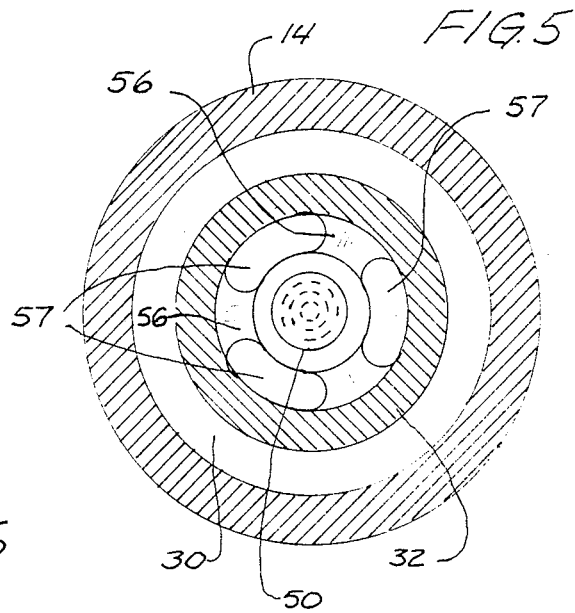

The tang 43 is surrounded at its upper end by an O-ring 45 that seals any air passage. The webs 42 form openings 42A which are part-annular. The openings 42A open into a chamber 46 that is defined in the interior of the intermediate or second stage impactor housing 32. A plate 47 closes off this chamber at its lower side. The plate 47 has an orifice 48 therein which also is centered on the axis 19, and is directly aligned above an impactor plate 50 again comprising electron microscope stud having a tang 51, which fits in an opening of a support plate 55. The tang 51 is also sealed with an O-ring 52. The support plate 55 is in turn supported relative to the base 33 on webs 56. As shown in FIG. 5, the webs 56 are spaced apart to provide for air passages 57 spaced annularly around the periphery of the plate 55, and these air passageways then lead into a lower chamber defined in the base sleeve member 33. The base sleeve member 33 is provided with a recess 60, that provides an overhanging shoulder which cooperates with a shoulder surface 61 formed as a step on from the boss 37 to support a two-piece filter holder shown at 62 that sandwiches or clamps a suitable filter 63 in place across the opening to a passageway 64. The passageway 64 leads to an outlet port and a line 65 which in turn is connected to a minor flow pump 66. The pump 66 provides a desired low flow capability to draw air through the receiver tube 27, and through the respective passageways 42A, 48 and 57, and then into passageway 64. These passageways are all closed from the chamber 22 and passageway 30, except through the opening in the nozzle 27.

Figure 1:
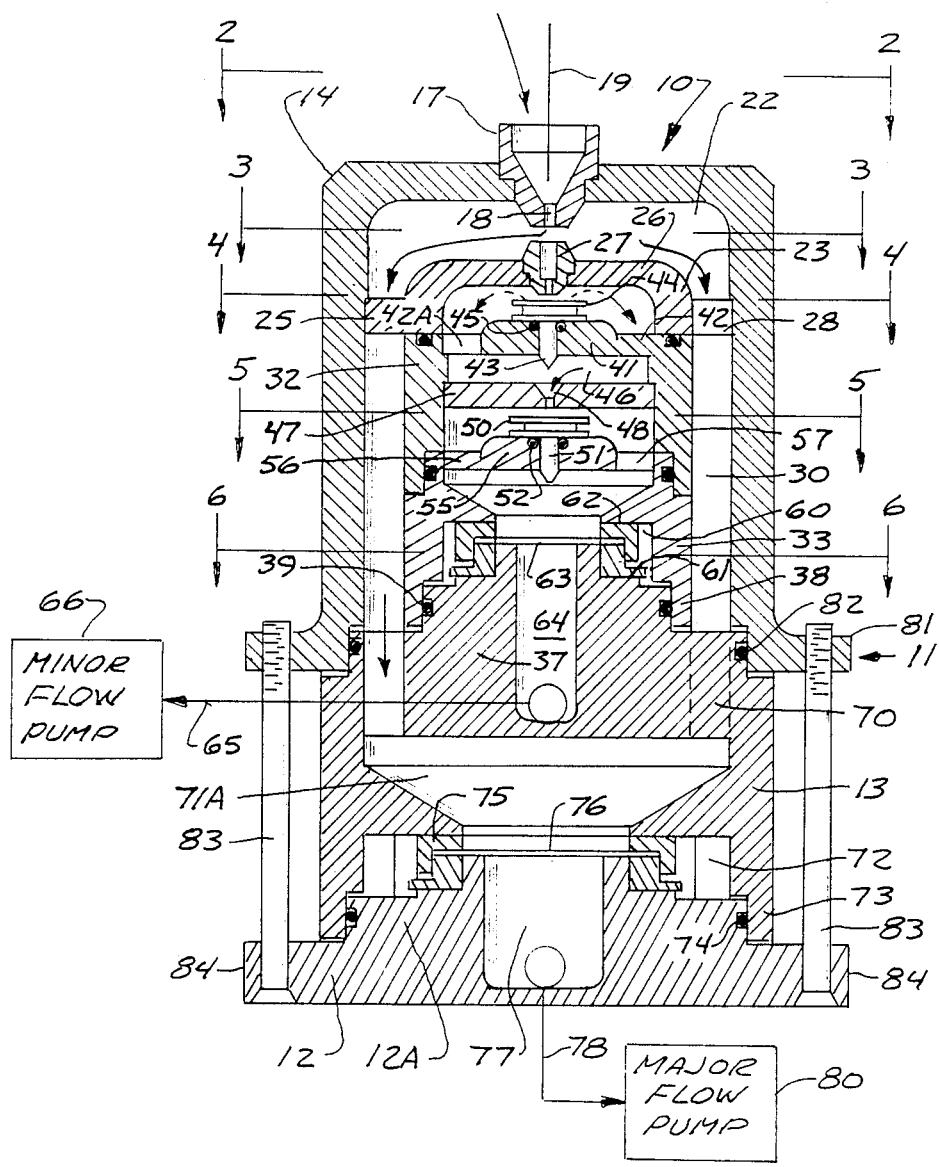
Figure 6:
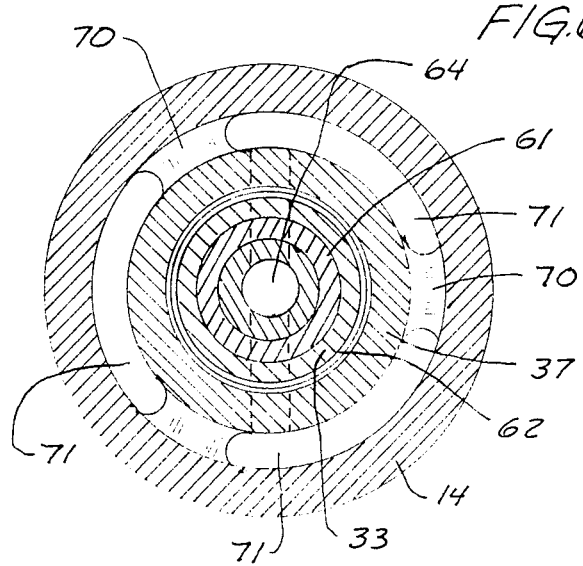

As shown in FIG. 6, the base 13 also supports the block member or boss 37 on webs 70 to define passageways 71, each of which is part-annular around the boss 37. The passageways 71 lead from passageway 30 into a chamber 71A formed on the lower part of the intermediate section 13. As can be seen in FIG. 1, the intermediate section 13 has a recess 72 defined on the lower side thereof, which forms a skirt 73 that is mounted around a boss portion 12A of the base 12 and sealed thereto with a suitable O-ring 74. The recess 72 is of size to permit a two-part filter holder indicated at 75 to be clamped between a lower shoulder surface of intermediate section 13 and an upper shoulder surface of the boss portion 12A, and to hold a filter 76 in position overlying a passageway 77. The passageway 77 is connected through a suitable port and line 78 to a major flow pump 80 of conventional design that provides for a desired, known flow of air, substantially larger than the minor flow, to be introduced through the nozzle 17 and then carried through the chamber 22, passageway 30, passageways 71, chamber 71A through the filter 76, passageway 77, conduit or line 78 and through the major flow pump.

The entire concentrating collector housing assembly is held together by clamping the outer housing 14 relative to the base 12 to engage the various shoulders provided. The housing 14 has ears 81 on opposite sides thereof, and also is recessed on its bottom side to fit around an outer diameter of the boss 37, and to be sealed with respect thereto by an O-ring 82. Suitable bolts or screws 83 pass through ears 84 on the boss 12, which align with the ears 81 on the housing 14 and the screws 83 are threaded into the ears 81 so that the parts can be drawn together. It should be noted that although some of the O-rings are not numbered, the parts 23 and 32 are sealed around their periphery where they meet, and the part 32 surrounds a boss section of the base 33 and is sealed thereto with an O-ring so that the air flow is directed properly.

The major flow pump, which could for example be any desired volume but typically is in the range of 1 cubic foot per minute causes a major flow of air inwardly through the nozzle 17, as generally indicated by arrows. The particles in the air will pass through the orifice 18 of the nozzle and partially into the chamber of the receiving tube 27. Because the major flow of air will be moved laterally as indicated by arrows, down through the passageways 28 into the passageway 30, and thus out to the major flow pump, the lighter particles will be carried with this major flow while the heavier particles will pass through the receiver tube 27 with the minor flow and will be impacted against the impactor plate 44. The flow through the receiver tube 27 will be controlled by the volume of the minor flow pump 66, which can be selected to be approximately 5% or less of the major flow.

The large particles therefore will be concentrated in a flow volume that is substantially smaller than the total flow volume, and consequently the volume of minor flow will have a larger number of large particles than the original air being sampled. If for example there is one particle per cubic foot above the cutoff size in the incoming air, and the minor flow is 1/20 of the major flow, there will be 20 times as many particles of the minor flow that will be impinging upon the impactor plate 44 for each cubic foot of air of minor flow. The impactor plate 44 is not greased, and the particles that impact on the plate 44 may bounce off, and be carried, generally as indicated by the dotted lines and arrows at the lateral sides of the impactor plate 44, through the passageways 42, and thus into the chamber 46. The flow will pass down through the orifice 48, where the flow will be accelerated again because of the Venturi effect of the orifice 48. The particles carried through the orifice 48 will impact on the second impactor plate 50, which may be covered with a layer of grease to insure that the particles adhere to the plate.

The minor flow will then continue on through the passageway 57, and through filter 63, passageway 64 and then out the minor flow pump 66.

In this way, the particles can be analyzed after the disassembly of the housing 14 by merely taking out the headed stud forming impactor plate plate 44 and placing it in an electron microscope. The same can be done with the plate 50.

The percentage of the major flow which constitutes the minor flow can be varied, and can be 1% or lower for example, so that the particle concentration factor can be quite high.

Figure 7:
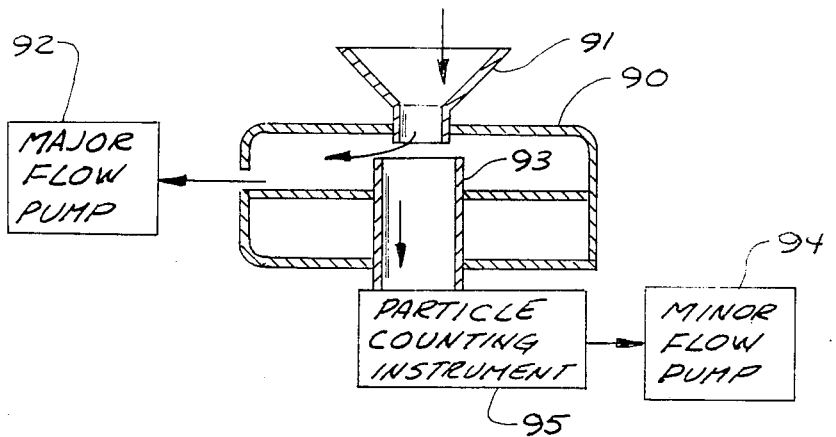

Schematically, in FIG. 7, a concentrating sampler is shown, which includes a housing 90, an inlet nozzle 91, through which a major flow generated by a major flow pump 92 enters. In this case, a receiver tube is shown schematically at 93, and a minor flow pump 94 is made to draw a minor flow, which is a selected percentage of the major flow, through a particle counting instrument 95, and then through the receiver tube 93 so that the minor flow carrying the larger particles, above the cutoff size will pass through a particle counting instrument for direct counting. This particle counting instrument can be an optical counter or other suitable particle counters that are known in the field.

Figure 8:
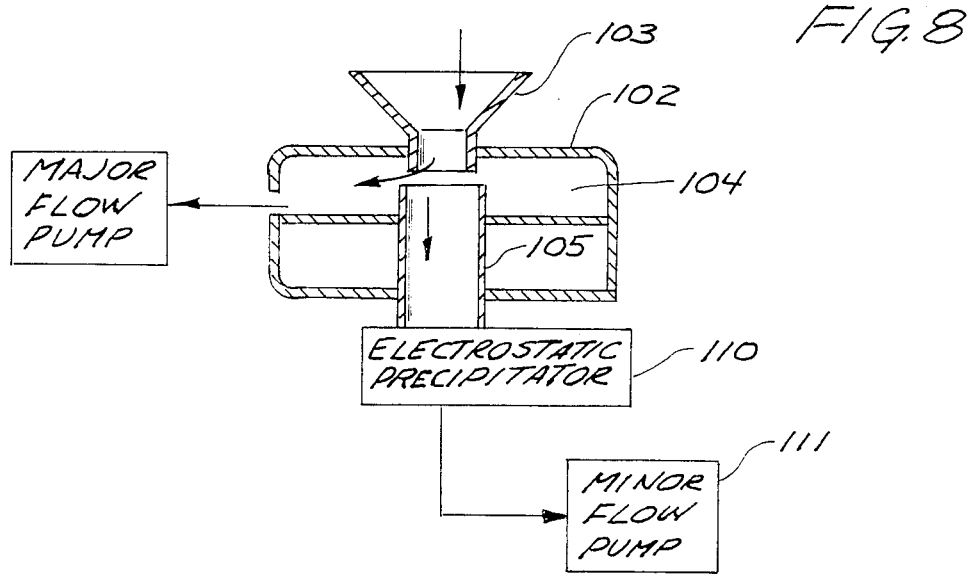

In FIG. 8, a further schematic representation is shown which uses an electrostatic precipitator. This would be used for collecting the particles and using the normal, known electrostatic precipitator functions for determining particle properties if necessary.

In this instance, a housing 102 has an inlet nozzle 103 leading to an interior chamber 104 in which a receiver tube 105 is mounted. A major flow pump is provided to draw air from the chamber 104, and the major flow carries the smaller particles laterally, while the larger particles will enter the receiver tube 105 and be carried through the electrostatic precipitator 110 along with the minor flow created by the minor flow pump 111. The electrostatic precipitator 110 can be used for collecting all of the particles passed through the receiver tube 105. The amount of concentration again depends on the proportions of the major flow and the minor flow, but the analysis can be made on a basis of more particles per unit volume. For example, if the concentration is 10 to 1, and the flow is 10 cubic feet per minute, the number of particles will be 10 times as great in the flow through the electrostatic precipitator (or through the particle counter in FIG. 7) as in the actual atmosphere that is being introduced into the nozzles.

Electrostatic precipitators can be used for analysis of many types of material in the air, for example, by causing the particles to adhere to a portion of the electrostatic precipitator. A heating current can be applied through the precipitator to heat, vaporize or pyrolize the particles and then a mass spectrometer or other appropriate analyzer used to analyze the vapor that is created and determine particle composition. Biological materials, such as bacteria, fungo-spores and viruses can be collected and analyzed. Also the presence of sulphates, nitrates and various hydrocarbons can be determined by collecting and analyzing the airborne particles.

The concentrating samplers shown are reliable, effective and low cost. They are easily used in clean rooms and can be placed in series for achieving the desired concentration of particles to be collected.

Although the present invention has been described with reference to preferred embodiments, workers skilled in the art will recognize that changes may be made in form and detail without departing from the spirit and scope of the invention.

What is claimed is:

1. A particle concentrating sampler and collector comprising a housing, said housing being made up of a plurality of sections, including a base, an intermediate section, and a top cap, said top cap having an interior and a top wall;
   a nozzle in said top wall centered along a central axis;
   a receiver tube mounted on the interior of said cap;
   a support for holding said receiver tube, said receiver tube having a central opening aligning with said central axis, and said support defining a space therearound on the interior of said cap for providing a first flow passage;
   means for removing a major flow of air through said nozzle and first flow passage;
   an impactor plate supported with respect to said support in alignment with said receiver tube; and
   means for establishing a minor flow through said receiver tube whereby the particles carried through said receiver tube strike the impactor plate.

2. The apparatus as specified in claim 1 wherein the impactor plate comprises a stud mounted plate, said stud being adaptible for mounting in an electron microscope.

3. The apparatus as specified in claim 1 wherein said support for said receiver tube comprises an annular housing, and the impactor plate is supported on annularly spaced webs extending from said support defining part-annular passageways for said minor flow, a nozzle plate positioned to receive flow from said passageways around said impactor plate, said nozzle plate having a central nozzle aligned with said axis, and a second impactor plate mounted to be aligned with said central nozzle for receiving particles passing through the nozzle of said nozzle plate, said means for establishing a minor flow providing a flow through said nozzle plate.

4. The apparatus as specified in claim 3 and a filter to filter the flow that passes through said nozzle plate, said filter being positioned so that the flow passes across the second impactor plate prior to passing through said filter.

5. The apparatus as specified in claim 4 wherein said filter is supported with respect to said intermediate support, said cap, said base, and said intermediate support being removably clamped together to form an assembly, and passageway means in said intermediate support for said major flow, means for providing said major flow connected downstream of said last-mentioned passageway means, and a filter between said last-mentioned passageway means and said means for establishing a major flow.

6. A particle concentrating collector comprising virtual impactor means including a housing having an inlet nozzle;

a receiver tube mounted on the interior of the housing and aligning with the inlet nozzle for receiving particle carrying inlet air, and being spaced from the inlet nozzle;

first outlet passageway means extending laterally of a space defined between the inlet nozzle and the receiver tube;

means for establishing a first major flow through said first outlet passageway;

means for establishing a minor flow through said receiver tube and through a second outlet passageway, said minor flow being a small percentage of the major flow; and means for collecting particles directly from said receiver tube comprising an impactor plate mounted on said housing immediately in line with said receiver tube, and a secondary passage receiving particles which bounce off said impactor plate for carrying said particles which bounce off the impactor plate in said minor flow.

* * * * *